United States Patent [19]

Hefner, Jr.

[11] Patent Number: 4,477,629

[45] Date of Patent: Oct. 16, 1984

[54] CYANATE-CONTAINING POLYMERS

[75] Inventor: Robert E. Hefner, Jr., Lake Jackson, Tex.

[73] Assignee: The Dow Chemical Company, Midland, Mich.

[21] Appl. No.: 517,861

[22] Filed: Jul. 27, 1983

[51] Int. Cl.³ .................... C07C 122/00; C08G 61/02; C08L 65/00; C08L 63/00

[52] U.S. Cl. ............................ 525/113; 260/453 AR; 260/453 P; 428/442; 525/328.2; 525/328.8; 525/374; 525/529; 528/99

[58] Field of Search ..................... 525/113, 529, 328.2, 525/328.8, 374; 528/99; 260/453 AR, 453 P

[56] References Cited

U.S. PATENT DOCUMENTS

| | | | |
|---|---|---|---|
| 3,448,079 | 6/1969 | Grigat et al. | 260/59 |
| 3,694,410 | 9/1972 | Oehmke | 260/47 R |
| 3,740,348 | 6/1973 | Grigat et al. | 260/453 AL |
| 3,755,402 | 8/1973 | Grigat et al. | 260/453 AR |
| 4,094,852 | 6/1978 | Sundermann et al. | 260/37 N |
| 4,273,889 | 6/1981 | Yamazaki et al. | 525/529 |

FOREIGN PATENT DOCUMENTS 1190184 4/1965 Fed. Rep. of Germany .
1218447 1/1971 United Kingdom .

*Primary Examiner*—V. P. Hoke
*Attorney, Agent, or Firm*—J. G. Carter

[57] ABSTRACT

New compositions of matter are disclosed which comprise (1) a cyanate-containing polymer or mixture thereof and optionally (2) a polycyanate or mixture thereof and/or (3) an epoxy resin. These compositions are thermosettable upon heating in the presence of suitable curing agents or catalysts.

8 Claims, No Drawings

CYANATE-CONTAINING POLYMERS

BACKGROUND OF THE INVENTION

The present invention pertains to novel thermosettable polymeric cyanates.

Thermosettable aromatic or bridged aromatic cyanates and the polytriazines resulting from curing of said cyanates are known in the prior art, for example, as taught by German Pat. Nos. 1,190,184; 1,195,764 and 1,720,740. In U.S. Pat. No. 3,694,410, a variety of polymeric dicyanates of the structure NC—O—R—O—CN with R being an oligomeric chain of bridged aromatic nuclei are taught. These dicyanates, however, suffer in reactivity upon curing due to the presence of the large bridging (R group) structures which inherently lower the density of curable cyanate groups. Further, the properties of these cured compositions become largely dependent upon said bridging (R group) structures rather than the polytriazine functionality, per se. As is emphasized in U.S. Pat. No. 4,094,852, the moisture sensitivity of the prior art polytriazines is unacceptably high.

The present invention provides polymeric cyanates of high reactivity and useful cured compositions via homopolymerization to the polytriazines. Copolymerization of these polymeric cyanates with difunctional cyanates of the prior art provides polytriazines with improved mechanical and thermal chemical properties and reduced moisture sensitivity. Copolymerization of these polymeric cyanates with epoxy resins provides useful cured compositions containing both triazine and oxazoline structures. These resins are useful in the preparation of laminates, castings, coatings and the like.

SUMMARY OF THE INVENTION

The present invention concerns a composition which comprises (A) from about 1 to 100, preferably from about 1 to about 75, most preferably from about 1 to about 50, percent by weight (pbw) of a cyanate-containing polymer or mixture of poly(cyanato)poly(alkenyl phenol)s represented by the formula:

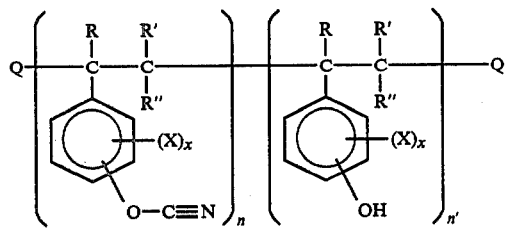

wherein each R, R' and R" is independently hydrogen or an alkyl group having from 1 to about 4 carbon atoms; each X is independently an alkyl group having from 1 to about 4 carbon atoms, chlorine or bromine; Q is independently a group derived from any suitable polymerization initiator or terminator,

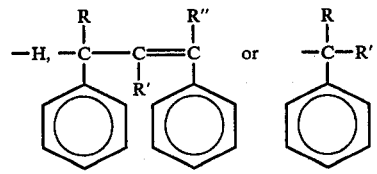

wherein each aromatic ring may contain any substituent group as those enumerated in formula I and each R, R' and R" is defined as in formula I; n has a value from about 5 to about 100, preferably from about 15 to about 80; n' has a value from zero to about 99, preferably from zero to about 5; and each x independently has a value from zero to 4; and (B) from zero to about 99, preferably from about 10 to about 90, most preferably from about 40 to about 85, pbw of an aromatic polycyanate or mixture of aromatic polycyanates represented by the formula:

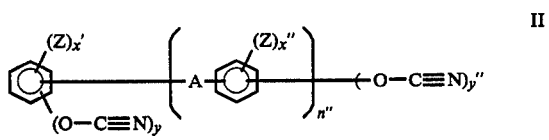

wherein each Z is independently hydrogen, an alkyl group having from 1 to about 4 carbon atoms, chlorine or bromine; A is a direct bond, a hydrocarbyl group having from 1 to about 10, preferably from 1 to about 4 carbon atoms, —S—, —S—S—, —O—,

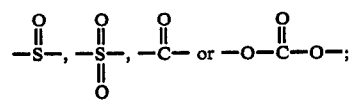

y has a value from zero to 5 when n" has a value of 1; y has a value from 2 to 5 when n" has a value of zero; x' has a value of 5 minus the value of y when n" has a value of 1; x' has a value of 6 minus the values of y plus y" when n" has a value of zero; x" has a value of 5 minus the value of y"; y" has a value of zero to 5; n" has a value of zero to 3; with the proviso that the sum of y and y" is always at least two; and (C) from zero to about 99, preferably from about zero to about 50, most preferably from about zero to about 25, pbw of an epoxy resin or mixture of epoxy resins represented by the formulas:

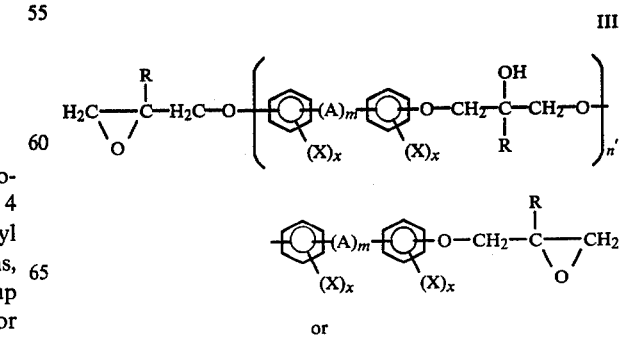

or

-continued

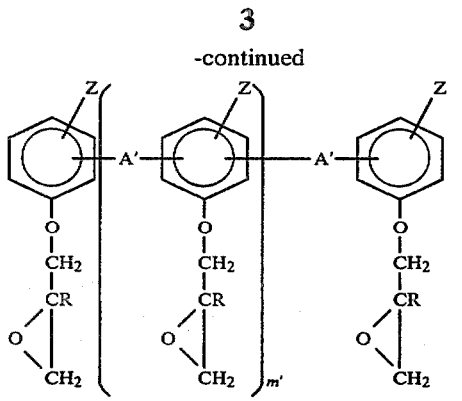

wherein R, X, Z, n', and x are as defined above; m' has a value of 0.01 to about 10, preferably from 0.01 to about 4, and each A is independently a hydrocarbyl group having from 1 to about 10, preferably from 1 to about 4 carbon atoms, —S—, —S—S—, —O—,

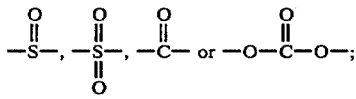

each A' is independently a hydrocarbyl group having from 1 to about 10, preferably from 1 to about 4 carbon atoms; each m has a value of zero or 1; wherein the pbw of the individual components is based upon the total weight of components A, B and C.

The present invention also pertains to the aforementioned composition when cured.

DETAILED DESCRIPTION OF THE INVENTION

The cyanate-containing polymer employed herein which are represented by formula I where n' is zero can be prepared by the reaction of stoichiometric or slight stoichiometric excess (up to about 20 percent) of a cyanogen halide and stoichiometric base per hydroxyl group.

Alternately, the method of Martin and Bauer described in Organic Synthesis, volume 61, pages 35–68(1983) and published by John Wiley and Sons can be used to generate the required cyanogen in situ from sodium cyanide and a halogen such as chlorine or bromine. The poly(cyanato)poly(alkenyl phenol)s employed herein which are represented by formula I where n' has a value of 1 to about 99 can be prepared by the reaction of less than stoichiometric cyanogen halide and correspondingly less than stoichiometric base per hydroxyl group. Suitable bases include both inorganic bases and tertiary amines, such as sodium hydroxide, potassium hydroxide, triethylamine, and the like. Suitable solvents include water, acetone, chlorinated hydrocarbons, ketones and the like. The cyanogen halides include cyanogen bromide and cyanogen chloride. Reaction temperatures of from about −40° to about 60° C. are operable with temperatures of −20° to 25° C. being preferred.

The average molecular weights of the cyanate-containing polymers vary as a function of the average molecular weight of the respective poly(alkenyl phenol) precursor as well as the extent of cyanation. The extent of cyanation may be varied such that each phenolic nucleus within the polymer chains is converted to a cyanate group (formula I wherein n' is zero) or only a portion of said phenolic hydroxyl groups are converted to cyanate groups (formula I wherein n' has a value of 1 to about 99).

In those instances where X is a halogen or an alkyl group, such products can be prepared by halogenating or alkylating the aromatic ring of the poly(alkenyl phenol) prior to use in a cyanation reaction. Useful products are prepared wherein all, a part, or none of the aromatic rings simultaneously bear halogen groups. Said products, wherein X is a halogen, are useful intermediates for fire retardant polymers.

The poly(alkenyl phenols) which are the starting materials for the products of the present invention can be purchased commercially from Maruzen Oil Co., Ltd., Tokyo, Japan as p-vinylphenol polymer Resin M or Resin MB.

If desired, the starting materials can be prepared by polymerizing an alkenyl phenol or mixture of alkenyl phenols by any suitable means such as heating in the presence or absence of a catalyst at a temperature of from about 25° C. to about 150° C. p-Vinylphenol readily homopolymerizes on standing at room temperature (25° C.). Other suitable alkenyl phenol precursors include m-vinylphenol and p-isopropenyl phenol. The aromatic polycyanates optionally employed herein which are represented by formula II can be prepared using methods taught by U.S. Pat. No. 4,094,852; German Pat. No. 1,190,184 which are incorporated herein by reference or the methods described herein.

The epoxy resins optionally employed herein which are represented by formulae III and IV can be prepared using methods taught by Lee and Neville in Handbook of Epoxy Resins (1967) McGraw-Hill Book Co.

The compositions of the present invention may be cured (polymerized) by heating from 70° to 350° C. or more, preferably by heating from 70° to 200° C. in the presence of 0.001 to 5 percent of a suitable catalyst. Operable catalysts include those disclosed in U.S. Pat. No. 4,094,852. Most preferred catalysts are cobalt naphthenate and cobalt octoate. Prepolymerization (B-staging) of the compositions of the present invention may be effected by using lower cure temperatures and/or shorter curing times. Curing of the prepolymerized resin may then be completed at a later time or immediately following prepolymerization to comprise a single curing step.

The compositions represented by formula I or by formulas I and II taken together polymerize through the formation of triazine structures to provide cured products. The progress of the polymerization can conveniently be followed by infrared spectrophotometry.

The compositions represented by formulae I, II, III and/or IV taken together or formulae I, III and/or IV taken together polymerize through the formation of both triazine and oxazoline structures to provide cured products.

The compositions of the present invention are useful in the preparation of castings, laminates, coatings and the like.

The following examples are illustrative of the invention but are not to be construed as to limiting the scope thereof in any manner.

EXAMPLE 1—Preparation of Cyanate-containing polymer

Cyanogen bromide (3.766 mole, 399 grams) was added to a reactor containing stirred acetone (250 milliliters) under a nitrogen atmosphere. The cyanogen bromide-acetone solution was cooled to −15° C. then poly(p-vinylphenol) (0.1069 mole, 374 grams) dissolved in chilled acetone (675 milliliters) was added to the reactor. The poly(p-vinylphenol) used was a commercial-grade product with an average molecular weight of 3500. The stirred solution was allowed to equilibrate at −5° C. then triethylamine (3.113 moles, 315 grams) was added to the reactor over a 170 minute (10200 s) period and so as to maintain the reaction temperature at −5° C. After completion of the triethylamine addition, the reactor was maintained at −5° C. for an additional 60 minutes (3600 s), followed by addition of the reaction product to chilled water (1 gallon) with agitation. After 15 minutes (900 s), the water and product mixture was multiply extracted with methylene chloride. The combined methylene chloride extracts were sequentially washed with dilute hydrochloric acid (5 percent), water, dilute hydrochloric acid, water and then dried over anhydrous magnesium sulfate. The dry methylene chloride extract was filtered and solvent removed by rotary evaporation under vacuum. Cyanate-containing polymer was recovered in 93.8 percent yield (423.9 grams) as a transparent light amber-colored solid. Infrared spectrophotometric analysis confirmed the product structure for the cyanate-containing polymer.

EXAMPLE 2—Preparation of Poly(cyanato)poly(alkenyl phenol)

Cyanogen bromide (1.10 mole, 116.52 grams) was added to a reactor containing stirred acetone (100 milliliters) under a nitrogen atmosphere. The cyanogen bromide-acetone solution was cooled to −15° C. then poly(p-vinylphenol) (0.0675 mole, 121.77 grams) dissolved in chilled acetone (500 milliliters) was added to the reactor. The poly(p-vinylphenol) used was a commercial grade product with an average molecular weight of 1800. The stirred solution was allowed to equilibrate at −5° C. then triethylamine (1.00 mole, 101.19 grams) was added to the reactor over a 103 minute (6180 s) period and so as to maintain the reaction temperature at −5° C. After completion of the triethylamine addition, the reactor was maintained at −5° C. for an additional 22 minutes (1320 s), followed by addition of the reaction product to chilled water (750 milliliters) with agitation. After 15 minutes (900 s), the water and product mixture was multiply extracted with methylene chloride. The combined methylene chloride extracts were sequentially washed with dilute hydrochloric acid (5 percent), water, dilute hydrochloric acid, water and then dried over anhydrous magnesium sulfate. The dry methylene chloride extract was filtered and solvent removed by rotary evaporation under vacuum. Cyanate-containing polymer was recovered in 92.5 percent yield (135.8 grams) as a transparent light amber-colored solid. Infrared spectrophotometric analysis confirmed the product structure for the cyanate-containing polymer.

COMPARATIVE EXPERIMENT A—Preparation of Bisphenol A Dicyanate

Cyanogen bromide (2.10 moles, 222.45 grams) was added to a reactor containing stirred acetone (350 milliliters) under a nitrogen atmosphere. The cyanogen bromide-acetone solution was cooled to −15° C. then Bisphenol A (1.00 mole, 228.30 grams) dissolved in chilled acetone (700 milliliters) was added to the reactor. The stirred solution was allowed to equilibrate at −5° C. then triethylamine (2.01 moles, 203.39 grams) was added to the reactor over a 125 minute (7500 s) period and so as to maintain the reaction temperature at −5° C. After completion of the triethylamine addition, the reactor was maintained at −5° C. for 30 minutes (1800 s), followed by addition of the reaction product to chilled water (650 milliliters) with agitation. After 15 minutes (900 s), the water and product mixture was multiply extracted with methylene chloride. The combined methylene chloride extracts were sequentially washed with dilute hydrochloric acid (5 percent), water, dilute hydrochloric acid, water and then dried over anhydrous magnesium sulfate. The dry methylene chloride extract was filtered and solvent removed by rotary evaporation under vacuum. Bisphenol A dicyanate was recovered in 91.6 percent yield (255.0 grams) as a white crystalline solid. Infrared spectrophotometric analysis confirmed the product structure for the dicyanate of Bisphenol A.

EXAMPLE 3

A pair of 12.0 in. × 12.0 in. (30.48 cm. × 30.48 cm.) woven fiberglass cloth pieces were equally impregnated with a solution prepared from cyanate-containing polymer (50.0 grams) of Example 1, methylene chloride (100 grams) and cobalt naphthenate (6.0 percent active) (0.166 grams). The fiberglass cloth used was a commercial-grade product treated with a proprietary coupling agent (Burlington 76-28 electrical laminating cloth) and had an average weight of 0.14 gram per square inch (0.9 g/cm$^2$). The pair of impregnated fiberglass cloths were allowed to dry for 24 hours at room temperature (25° C.) followed by prepolymerization (B-staging) in a vented, forced-air, convection-type oven for 10 minutes (600 s) at 70° C., 15 minutes (900 s) at 100° C., then 8 minutes (480 s) at 150° C. Each cloth was cooled, found to be tack-free at room temperature and then cut to provide eight 6 in. × 6 in. (15.24 cm. × 15.24 cm.) pieces. The pieces were stacked into a 6 in. × 6 in. × 1/16 in. (15.24 cm. × 15.24 cm. × 0.15275 cm.) stainless steel frame and placed between stainless steel plates which had been coated with a silicone mold release. The plates were loaded into a 150° C. hot press (Pasadena Hydraulics Inc., Model P-215) and maintained for 10 minutes (600 s) at 100 psi (689.48 kPa), 5 minutes (300 s) at 2000 psi (13790 kPa), then 10 minutes (600 s) at 5000 psi (34474 kPa). The temperature was then increased to 177° C. and this temperature was maintained for 1.0 hour (3600 s) with the 5000 psi (34474 kPa). After this time, a 6 in. × 6 in. × 1/16 in. (15.24 cm. × 15.24 cm. × 0.15275 cm.) light amber-colored, semitransparent, rigid laminate was recovered and cut to provide a set of three 1.0 in. × 3.0 in. × 1/16 in. (2.54 cm. × 7.62 cm. × 0.15875 cm.) flexural strength test pieces. The flexural strength test pieces were post-cured at 200° C. for 2.0 hours (7200 s) and then tested on an Instron machine with standard methods, (ASTM D-790 modified). the Instron machine was set at a 2 inch span, 0.05 inch per minute crosshead speed and 0.5 inch per minute chart speed. The Barcol hardness value is on the 934-1 scale. The results are reported in Table I.

EXAMPLE 4

A pair of 12.0 in. × 12.0 in. (30.48 cm. × 30.48 cm.) woven fiberglass cloth pieces were equally impregnated with a solution prepared from cyanate-containing polymer (10.0 grams) of Example 1, Bisphenol A dicyanate (40.0 grams) of Comparative Experiment A, methylene chloride (100 grams) and cobalt naphthenate (6.0 percent active) (0.166 grams). Prepolymerization (B-staging), laminate fabrication, pressing, and mechanical property testing were completed using the method of Example 3, with the single exception that prepolymerization at the 150° C. temperature was increased to 10 minutes (600 s) to provide tack-free cloth at room temperature. The laminate thus obtained was rigid, light amber-colored and semi-transparent. The results are reported in Table I.

COMPARATIVE EXPERIMENT B

A pair of 12.0 in. × 12.0 in. (30.48 cm. × 30.48 cm.) woven fiberglass cloth pieces were equally impregnated with a solution prepared from Bisphenol A dicyanate (50.0 grams) of Comparative Experiment A, methylene chloride (100 grams) and cobalt napthenate (6.0 percent active) (0.166 grams). Prepolymerization (B-staging), laminate fabrication, pressing, and mechanical property testing were completed using the method of Example 3, with the single exception that prepolymerization at the 150° C. temperature was increased to 20 minutes (1200 s) to provide a tack-free cloth at room temperature. The laminate thus obtained was rigid, white colored and semi-transparent. The results are reported in Table I.

TABLE I

|  | Example 3 | Example 4 | Comparative Experiment B |
|---|---|---|---|
| Barcol Hardness | 51 | 64 | 54 |
| Flexural Strength, psi | $32.0 \times 10^3$ | $51.6 \times 10^3$ | $49.3 \times 10^3$ |
| kPa | $220.6 \times 10^3$ | $355.8 \times 10^3$ | $340 \times 10^3$ |
| Flexural Modulus, psi | $2.98 \times 10^6$ | $3.39 \times 10^6$ | $2.74 \times 10^6$ |
| kPa | $20.55 \times 10^6$ | $23.37 \times 10^6$ | $18.89 \times 10^6$ |

EXAMPLE 5

A set of three 1.0 in. × 3.0 in. × 1/16 in. (2.54 cm. × 7.62 cm. × 0.15875 cm.) flexural strength test pieces were cut from the laminates of Example 3, Example 4 and Comparative Experiment B, respectively, and then post-cured at 200° C. for 2.0 hours (7200 s). Each laminate test piece was weighed, then all were immersed under water and maintained therein for 10 days (864,000 s) at a temperature of 25° C. On the fourth day (345,600 s) of exposure to the water, the test pieces were removed, blotted, weighed, and then replaced back into the water. After 10 days (864,000 s) of exposure, the test pieces were removed and again weighed. All test pieces were kept moist just prior to testing on an Instron machine using the method of Example 3. The results are reported in Table II where comparisons against the unexposed (initial) properties are also provided.

TABLE II

|  | Example 3 | Example 4 | Comparative Experiment B |
|---|---|---|---|
| Barcol Hardness |  |  |  |
| initial | 51 | 64 | 54 |
| exposed | 52 | 67 | 41 |
| (percent change) | (+1.96) | (+4.69) | (−24.07) |
| Flexural Strength |  |  |  |
| initial, psi | $32.0 \times 10^3$ | $51.6 \times 10^3$ | $49.3 \times 10^3$ |
| kPa | $220.6 \times 10^3$ | $355.8 \times 10^3$ | $339.9 \times 10^3$ |
| exposed, psi | $32.4 \times 10^3$ | $53.2 \times 10^3$ | $42.1 \times 10^3$ |
| kPa | $223.4 \times 10^3$ | $366.8 \times 10^3$ | $290.3 \times 10^3$ |
| (percent change) | (+1.25) | (+3.10) | (−14.60) |
| Flexural Modulus |  |  |  |
| initial, psi | $2.98 \times 10^6$ | $3.39 \times 10^6$ | $2.74 \times 10^6$ |
| kPa | $20.55 \times 10^6$ | $23.37 \times 10^6$ | $18.89 \times 10^6$ |
| exposed, psi | $3.11 \times 10^6$ | $3.45 \times 10^6$ | $2.70 \times 10^6$ |
| kPa | $21.44 \times 10^6$ | $23.79 \times 10^6$ | $18.62 \times 10^6$ |
| (percent change) | (+.36) | (+1.77) | (−1.46) |
| Percent Weight Gain |  |  |  |
| 4 days (345600 s) of exposure | 0.98 | 0.39 | 0.83 |
| 10 days (864000 s) of exposure | 1.33 | 0.65 | 1.52 |

EXAMPLE 6

The solutions of Example 3, Example 4, and Comparative Experiment B, respectively, were again each prepared. A 1 gram sample of each solution was devolatilized to remove methylene chloride solvent then all were cured at 177° C. for 1 hour (3600 s) and 200° C. for 2 hours (7200 s). A portion of each cured polytriazine product was used for thermal gravimetric analysis (TGA). The lower temperature limit was 50° C. while the upper temperature limit was 950° C. A heating rate of 50° C. per minute (0.83° C./s) was used. All analysis was performed under a nitrogen atmosphere. The results are reported in Table III.

TABLE III

| Temperature (°C.) | Percent of Original Weight | | |
|---|---|---|---|
|  | Example 3 | Example 4 | Comparative Experiment B |
| 400 | 98.1 | 99.2 | 99.6 |
| 450 | 81.2 | 87.8 | 93.8 |
| 500 | 58.6 | 58.4 | 59.8 |
| 550 | 54.4 | 52.0 | 50.8 |
| 600 | 51.0 | 47.4 | 45.9 |
| 650 | 48.2 | 44.9 | 42.6 |
| 700 | 46.1 | 43.2 | 39.3 |
| 750 | 44.2 | 42.0 | 35.8 |
| 800 | 42.8 | 41.2 | 31.9 |
| 850 | 41.7 | 40.4 | 28.1 |
| 900 | 40.4 | 40.0 | 24.5 |
| 950 | 38.8 | 39.7 | 21.2 |

EXAMPLE 7

A pair of 12.0 in. × 12.0 in. (30.48 cm. × 30.48 cm.) woven fiberglass cloth pieces were equally impregnated with a solution prepared from cyanate-containing polymer (25.0 grams) of Example 1, diglycidyl ether of Bisphenol A having an epoxide equivalent weight (EEW) of 184.5 (25.0 grams), methylene chloride (100 grams) and cobalt naphthenate (6.0 percent active) (0.166 grams). Prepolymerization (B-staging) time was 10 minutes (600 s) at 70° C. to provide cloth which was only slightly tacky at room temperature. Laminate fabrication, pressing, and mechanical property testing were completed using the method of Example 3. The laminate thus obtained was rigid, light yellow-colored and non-transparent. The results are reported in Table IV.

TABLE IV

|  | Example 7 |
|---|---|
| Barcol Hardness | 51 |
| Flexural Strength, psi | 38.8 × 10³ |
| kPa | 267.5 × 10³ |
| Flexural Modulus, psi | 2.89 × 10⁶ |
| kPa | 19.93 × 10⁶ |

I claim:

1. A composition which comprises
(A) from about 1 to 100 percent by weight (pbw) of a cyanate-containing polymer or mixture of cyanate-containing polymers represented by the formula:

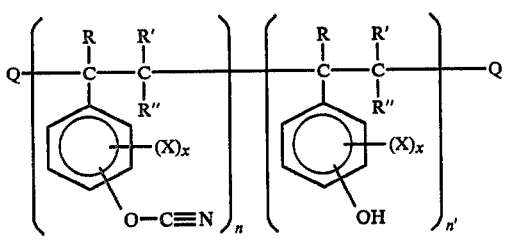
I wherein each R, R' and R" is independently hydrogen or an alkyl group having from 1 to about 4 carbon atoms; each X is independently an alkyl group having from 1 to about 4 carbon atoms, chlorine or bromine; Q is independently a group derived from any suitable polymerization initiator or terminator,

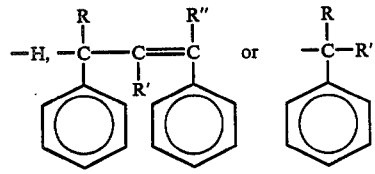

wherein each aromatic ring may contain any substituent group as those enumerated in formula I and each R, R' and R" is defined as in formula I; n has a value from about 5 to about 100; n' has a value from zero to about 99; and each x independently has a value from zero to 4; and (B) from zero to about 99 pbw of an aromatic polycyanate or mixture of aromatic polycyanates represented by the formula:

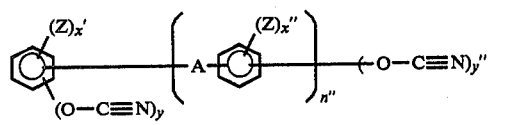
II wherein each Z is independently H-, an alkyl group having from 1 to about 4 carbon atoms, chlorine or bromine; A is a direct bond, a hydrocarbyl group having from 1 to about 10 carbon atoms, —S—, —S—S—, —O—,

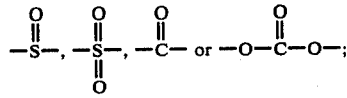

y has a value from zero to 5 when n" has a value of 1; y has a value from 2 to 5 when n" has a value of zero; x' has a value of 5 minus the value of y when n" has a value of 1; x' has a value of 6 minus the values of y plus y" when n" has a value of zero; x" has a value of 5 minus the value of y"; y" has a value of zero to 5; n" has a value of zero to 3; with the proviso that the sum of y and y" is always at least two; and (C) from zero to about 99 pbw of an epoxy resin or mixture of epoxy resins represented by the formulas:

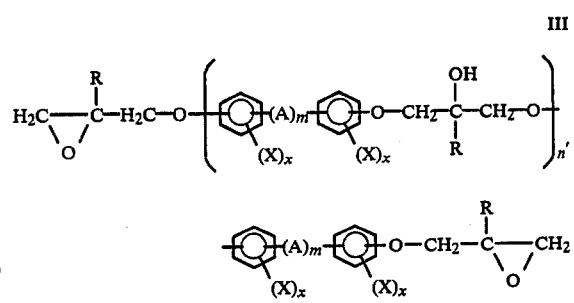
III

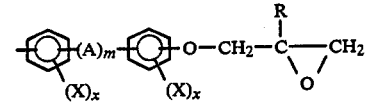

or

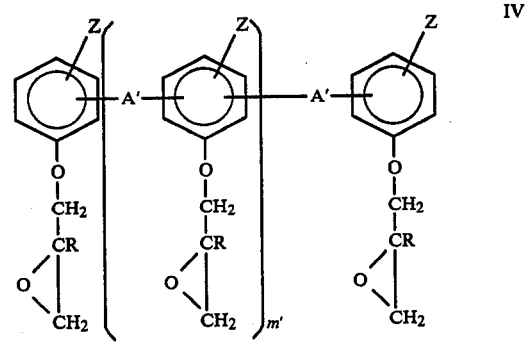
IV wherein R, X, Z, n', and x are as defined above; m' has a value of 0.01 to about 10, and each A is independently a hydrocarbyl group having from 1 to about 10 carbon atoms, —S—, —S—S—, —O—,

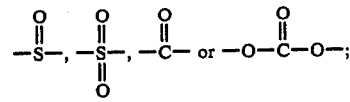

each A' is independently a hydrocarbyl group having from 1 to about 10 carbon atoms; each m has a value of zero or 1; wherein the pbw of the individual components is based upon the total weight of components A, B and C.

2. A composition of claim 1, wherein
(i) component A is present in quantities of from about 1 to about 75 pbw;
(ii) component B is present in quantities of from about 10 to about 90 pbw;

(iii) component C is present in quantities of from about zero to about 50 pbw;

(iv) in formula I, n has a value from about 15 to about 80, n' has a value from zero to about 5;

(v) in formula III, when A is a hydrocarbyl group it has from 1 to 4 carbon atoms, n' has a value from zero to about 5 and each R is hydrogen; and (vi) in formula IV, each R is hydrogen and A' has from 1 to about 4 carbon atoms, and m' has a value from 0.01 to about 4.

3. A composition of claim 2 wherein (i) component A is present in quantities of from about 1 to about 50 pbw;

(ii) component B is present in quantities of from about 40 to about 85 pbw;

(iii) component C is present in quantities of from about zero to about 25 pbw.

4. A composition of claims 1, 2 or 3 wherein (i) in Formula I, each R, R' and R" are hydrogen and x has a value of zero;

(ii) in Formula II, when component B is present, A is an isopropylidene group, each Z is hydrogen, n" has a value of 1 and y and y" each have a value of 1; and (iii) component C, when present, is represented by formula III wherein each R is hydrogen, each A is an isopropylidene group, m has a value of 1, n' has a value of from zero to about 5 and each x has a value of zero.

5. A composition of claims 1, 2 or 3 wherein (i) each R, R' and R" is hydrogen, X is bromine and x has a value of 1 or 2;

(ii) in formula II, when component B is present, A is an isopropylidene group, at least one Z is bromine and the other Z's are hydrogen, n" has a value of 1 and y and y" each have a value of 1; and (iii) component C, when present, is represented by formula III wherein each R is hydrogen, each A is an isopropylidene group, each X is bromine, m has a value of 1, n' has a value of from zero to about 5 and each x has a value of 2.

6. A product resulting from mixing a composition of claims 1, 2 or 3 with an effective quantity of a suitable curing agent or catalyst or mixture of such curing agents or catalysts and subjecting the mixture to curing conditions.

7. A product resulting from mixing a composition of claim 4 with an effective quantity of a suitable curing agent or catalyst or mixture of such curing agents or catalysts and subjecting the mixture to curing conditions.

8. A product resulting from mixing a composition of claim 5 with an effective quantity of a suitable curing agent or catalyst or mixture of such curing agents or catalysts and subjecting the mixture to curing conditions.

* * * * *

UNITED STATES PATENT AND TRADEMARK OFFICE
CERTIFICATE OF CORRECTION

PATENT NO. : 4,477,629
DATED : October 16, 1984
INVENTOR(S) : Robert E. Hefner, Jr.

It is certified that error appears in the above—identified patent and that said Letters Patent is hereby corrected as shown below:

Col. 3, line 48; insert --halide-- between "cyanogen" and "in".

Col. 3, line 50; delete "poly(cyanato)poly(alkenyl phenol)" and insert therefor --cyanate-containing polymer--.

Col. 6, line 65; change "the" to --The--.

Col. 10, line 64; change "1," to --1--.

Signed and Sealed this

Thirteenth Day of August 1985

[SEAL]

Attest:

DONALD J. QUIGG

Attesting Officer

Acting Commissioner of Patents and Trademarks